United States Patent [19]

Yuspa

[11] Patent Number: 5,616,471

[45] Date of Patent: Apr. 1, 1997

[54] EFFECTS OF GROWTH FACTORS ON HAIR FOLLICLE CELL PROLIFERATION AND RELEASE OF COLLAGENOLYTIC FACTORS

[75] Inventor: Stuart H. Yuspa, Bethesda, Md.

[73] Assignee: The United States of America as represented by the Department of Health and Human Services, Washington, D.C.

[21] Appl. No.: 650,572

[22] Filed: Feb. 4, 1991

Related U.S. Application Data

[63] Continuation-in-part of Ser. No. 48,537, May 6, 1987.

[51] Int. Cl.$^6$ .............................. A01N 1/02; C12N 5/00; A61K 38/00; C07K 1/00
[52] U.S. Cl. ............................ 435/29; 435/243; 435/244; 514/21; 514/880; 530/356; 623/15
[58] Field of Search ................................ 435/29, 240.23, 435/240.21, 240.243, 260, 243, 244; 514/880, 21; 530/356; 623/15

[56] References Cited

PUBLICATIONS

Weinberg, et al., "Growth Factor Effects on Cultured Hair Follicles" J. Investigative Dermatology 94:589 (Apr. 1990).

Rogers et al J Investigative Dermatology vol. 89 No. 4 pp. 369–379.

*Primary Examiner*—Donald E. Czaja
*Assistant Examiner*—Jane Williams Elkin
*Attorney, Agent, or Firm*—NIH Office of Technology Transfer

[57] ABSTRACT

The present invention relates to methods for detecting the effects of selected growth factors and pharmaceuticals on the growth and development of hair follicles by assaying hair follicle cell proliferation and cellular collagenolytic factor secretion. In particular, isolated hair follicle cells maintained as intact functioning folliculoids are embedded in a three-dimensional culture system, and exposed to the chemical agent of choice. The effect of this agent can then be determined with respect to its ability to modify cellular proliferation or secretion of proteolytic factors. Each determination involves the use of a separate assay.

27 Claims, 6 Drawing Sheets

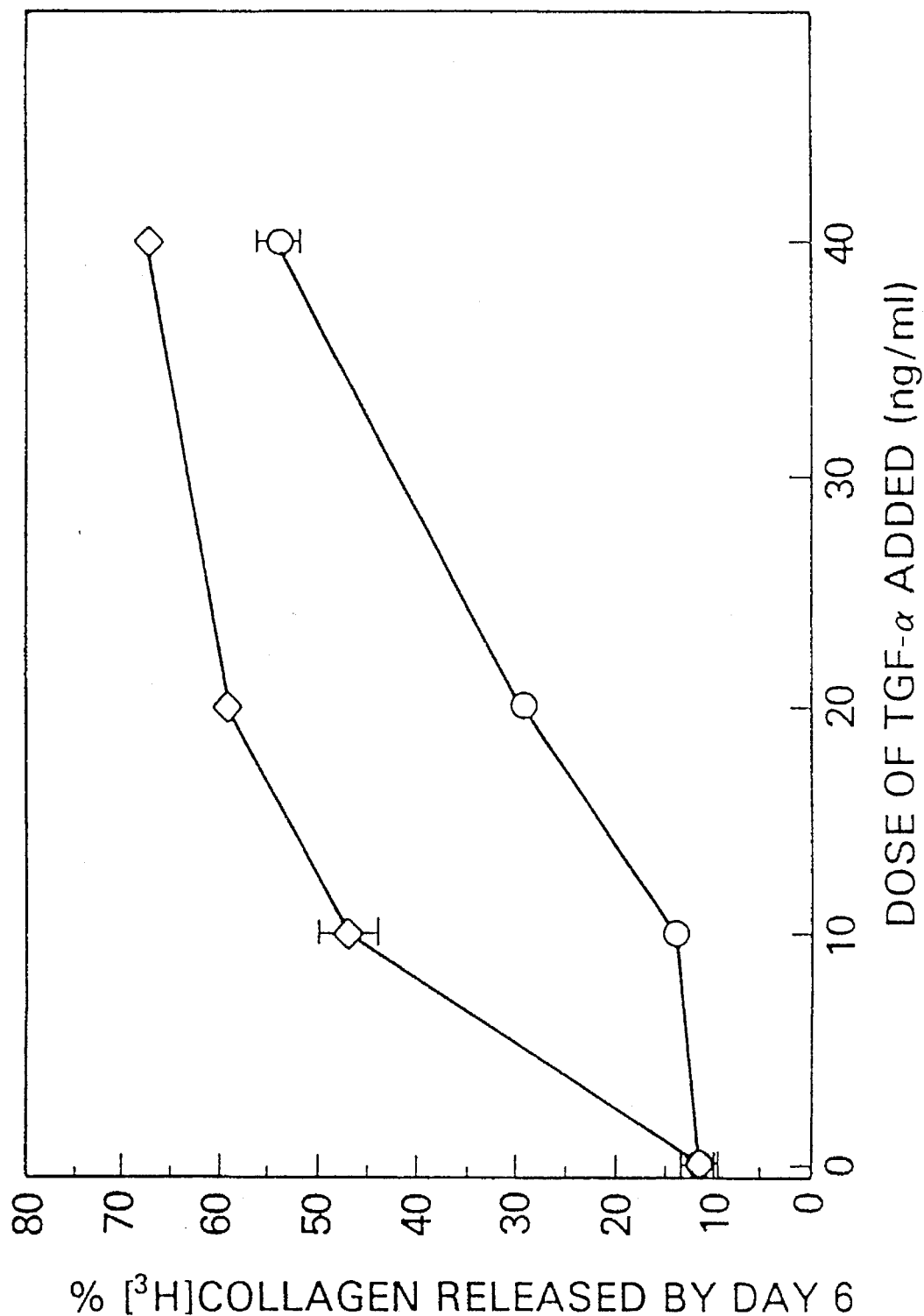

EFFECTS OF GROWTH FACTORS ON HAIR FOLLICLE CELL PROLIFERATION AND RELEASE OF COLLAGENOLYTIC FACTORS

The present application is a continuation-in-part of U.S. patent application Ser. No. 07/048,537 filed, on May 6, 1987, hereby incorporated in its entirety by reference.

BACKGROUND OF THE INVENTION

1. Technical Field

The present invention relates to methods for detecting the effects of selected growth factors and pharmaceuticals on hair follicle cell proliferation and cellular collagenolytic factor secretion.

2. Background Information

Hair follicle morphogenesis in developing skin is a complex process involving induction of endophytic epidermal buds by underlying mesenchyme, and proliferation, migration, and differentiation of the epithelial component to form a three dimensional structure spanning the deep dermis to the epidermal surface. The activity of this organ cycles throughout the lifetime of the animal as the active (anagen) hair follicle regresses (catagen phase) and enters a resting phase (telogen). A process similar to morphogenesis occurs each time the telogen hair follicle is induced to re-enter anagen. Specific signals mediating hair follicle induction, regression and reactivation have not yet been identified.

Since substantial proliferative activity is required to produce a mature hair follicle, it is likely that the differential expression of growth factors and their receptors is one important mechanism which controls these processes. A number of growth factors and growth factor receptors, including transforming growth factor beta (TGF-$\beta$) and receptors for epidermal growth factor (EGF), have been localized to specific regions of the hair bulb or surrounding stroma at various stages of hair growth, and differential expression of growth factor mRNA for TGF-$\beta$1 and TGF-$\beta$2 has been detected in developing follicles of embryonic skin (Green et al., *J. Invest Dermatol.* 83: 118–23 (1984), Heine et al., *J. Cell Biol.* 105: 2861–76 (1987), Lehnert et al., *Development* 104: 263–73 (1988) and Pelton et al., *Development* 106: 759–67 (1989)). Thus, these factors may be involved in hair follicle growth and differentiation.

In mouse skin, the dermis expands and contracts in thickness in parallel with the hair growth cycle ((Sengel, P., *Morphogenesis of Skin* (Cambridge Univ. Press, Cambridge (1976)). As it grows, the anagen hair follicle migrates through a dermis which is simultaneously expanding to several times its original thickness. This migration of the developing hair follicle through the stromal component during initial formation and in later anagen phases is reminiscent of tumor invasion. On the basis of these observations, it was proposed that collagenases and other proteases may be important in follicle invasion into the deeper dermis (Rogers, et al., *J. Invest. Dermatol.* 89: 369–79 (1987)), as well as in the remodeling observed during involution of the hair bulb in catagen.

A limiting factor in the analysis of hair follicle growth and development has been the lack of a suitable in vitro model to study these events in a controlled setting. Several cell culture models employing dissociated follicle cells do not support the production of hair specific keratins or other features of follicle differentiation (Imcke et al., *J Am. Acad. Dermatol.* 17: 779–86 (1987), Jones et al., *J. Invest. Dermatol.* 90: 58–64 (1988), Limat et al., *J. Invest. Dermatol.* 87: 485–88 (1986), Noser et al., *In vitro Cell Dev. Biol.* 23: 541–45 (1987) and Weterings et al., *Br. J. Dermatol.* 104: 1–5 (1981)). The present inventors have described methods for the enzymatic isolation of intact pelage hair follicles from newborn mouse skin and their maintenance in a 3-dimensional type I collagen gel (Rogers et al., *J. Invest. Dermatol.* 89: 369–79 (1987)). Such follicles, when reisolated from culture after 7 days, will establish a haired skin when tested in a nude mouse graft model (Rogers et al., supra). When cultured as 3-dimensional organoids, mouse follicles produce a 62 kD cytokeratin band distinct from proteins produced by interfollicular epidermal cells (Rogers et al., supra). The initial studies with this model indicated that follicle cell proliferation was stimulated by epidermal growth factor and cholera toxin, suggesting that this system was useful to analyze responses of follicle cell subpopulations to cytokines. Furthermore, EGF caused follicle cell-mediated lysis of the collagen gel matrix, presumably by stimulating secretion of a collagenase. Thus, this model promised to reveal information regarding the regulation of follicle invasion as well.

The present invention relates to a further analysis of selected growth factors, and pharmaceuticals individually and in combination, with regard to their abilities to stimulate proliferation and collagenase secretion in cultured follicle organoids. The results provide new information which may be relevant to the control of growth and invasion during hair follicle development in vivo.

SUMMARY OF THE INVENTION

The present invention relates methods of detecting the effects of selected growth factors and pharmaceuticals on follicle cell proliferation and cellular release of collagenolytic factors. A three-dimensional culture model which includes a type I collagen gel is utilized for this purpose.

In particular, the present invention relates to a method for detecting the ability of a chemical agent to stimulate follicle cell proliferation comprising the steps of:

i) isolating follicles from dermis;

ii) plating a layer of semi-solid medium on a support;

iii) mixing said follicles with a semi-solid medium, and plating said mixture over the layer of step (ii), thereby creating a three-dimensional culture system;

iv) adding said chemical agent to a liquid placed over the semi-solid medium of step (iii);

v) pulsing said three-dimensional culture system with a radio-labeled compound which can detect DNA synthesis;

vi) releasing said follicle cells from the layer in which they are embedded, by enzymatic digestion; and vii) measuring the amount of cellular proliferation by determining the amount of said radio-labeled compound or reagent incorporated into the DNA of said cells.

The chemical agent referred to above may be a growth factor, for example, TGF-$\alpha$, TGF-$\beta$1, TGF$\beta$2, EGF, or cholera toxin. The agent may also be a pharmaceutical. The radio-labeled compound may be, for example, a DNA precursor such as [$^3$H]thymidine. Furthermore, compounds other than radio-labeled compounds can be utilized such as, for example, compounds attached to a fluorescent label or compounds which have any other marker or label attached and which can detect DNA synthesis. The layer of step (ii) may comprise collagen.

The present invention also relates to a method of detecting the effect of a chemical agent on the release of lytic factors from a follicle cell comprising the steps of:

i) isolating follicles from dermis;
  ii) plating a layer of a semi-solid medium comprising a radio-labeled agent on a support;
  iii) mixing said follicles with a semi-solid medium, and plating said mixture over said layer of step (ii), thereby creating a three-dimensional culture system;
  iv) adding said chemical agent to a liquid medium placed over the semi-solid medium;
  v) determining the percentage of the radio-labeled agent released from said layer of step (ii) thereby determining the ability of said follicle cells to release lytic factors.

The chemical agent may be, for example, a growth factor or a pharmaceutical. Such growth factors include, for example, TGF-α, TGF-β1, TGF-β2, EGF, and cholera toxin. The radio-labeled agent of step (ii) may be, for example, [$^3$H]collagen. However, other compounds could be utilized such as compounds containing or bound to a fluorescent label or compounds bound to another type of marker. The layer of step (ii) may comprise collagen. Furthermore, the lytic factor of step (v) may be, for example, collagenolytic.

The present invention also relates to chemical agent which stimulates follicle cell proliferation according to the first method described above. The agent may be, for example, a pharmaceutical or growth factor.

Moreover, the present invention also relates to a chemical agent which effects the release of lytic factors from a follicle cell according to the second method described above. The chemical agent may be, for example, a pharmaceutical or a growth factor.

All U.S. patents and publications referred to herein are hereby incorporated by reference.

BRIEF DESCRIPTION OF THE DRAWINGS

FIG. 6 shows the synergistic effects of growth factors on release of collagenolytic activity from hair follicle cells: dose studies. The protocol was similar to that of FIG. 5. Cultures were exposed to varying doses of TGF-α alone (o) or with 1 ng/ml TGF-β (◊) and the % of [$^3$H]collagen released after 6 days was calculated. Error bars represent range of duplicate samples.

DETAILED DESCRIPTION OF THE INVENTION

Figure 1:
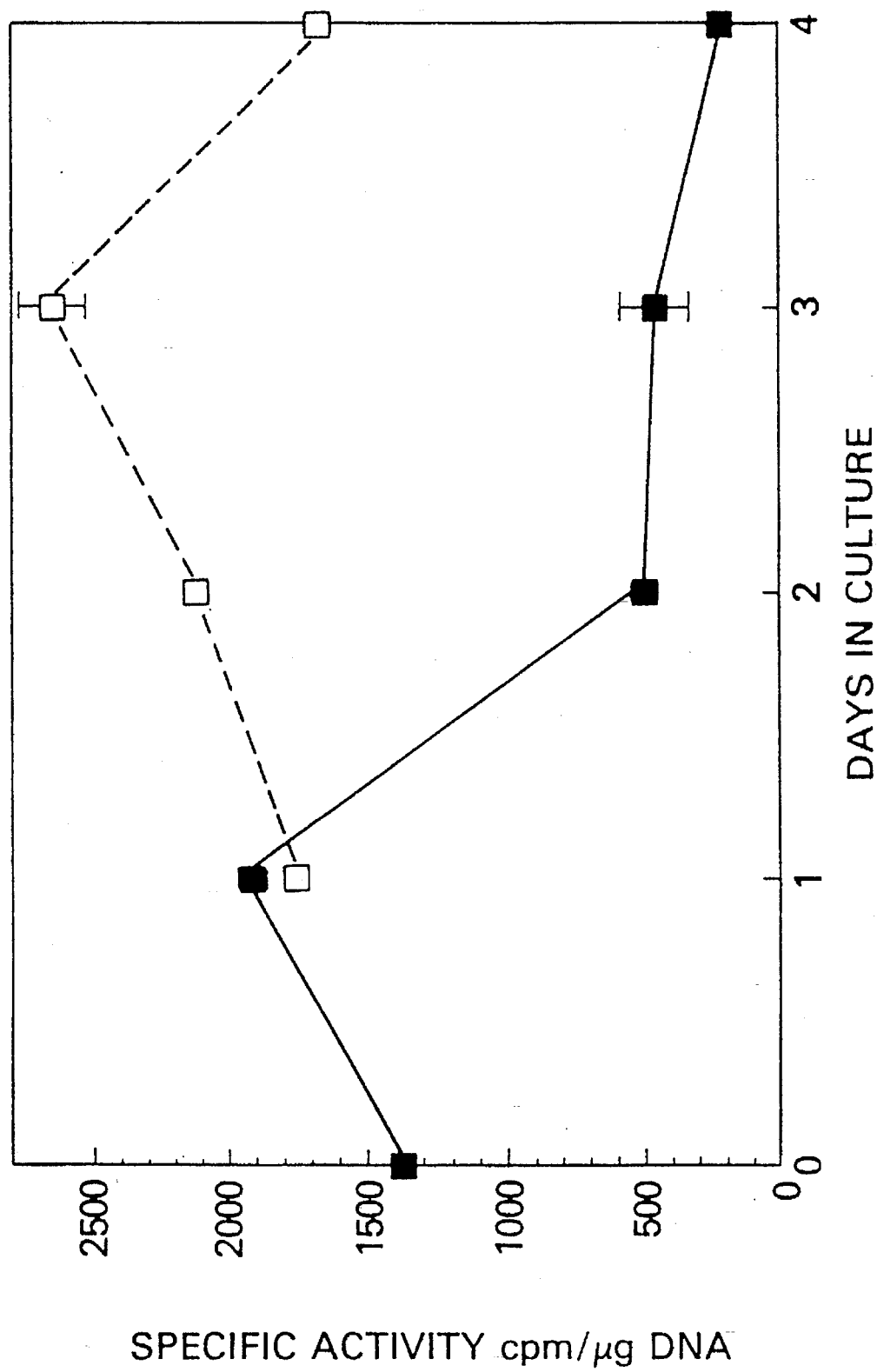
FIG. 1 shows the effect of plating density on time course of thymidine incorporation. Hair follicles isolated from an entire newborn mouse dermis were plated in the top collagen gel of each 60 mm dish (closed squares) or at one-third density (open squares). All cultures were fed daily with Medium 199 containing 8% FBS. Each day dishes were pulse-labelled with [$^3$H]thymidine (5 µCi/ml) for 2 hours, and the follicles were then released from the gel by collagenase digestion, washed and the pellets frozen. At termination of the timepoints, the frozen pellets were analyzed for DNA content and incorporation of label into DNA. Error bars represent the range of duplicate dishes.

The present invention relates to methods for detecting the effects of growth factors or other additives on follicle cell proliferation and cellular release of collagenolytic factors. The method involves the use of a 3-dimensional culture system. Basically, the purpose of the development of this culture system was to maintain the 3-dimensional structure and cell interactions which are likely to be important in normal follicle physiology.

The first step in carrying out the methods of the present invention involves the isolation of intact hair follicles from skin where hair follicles are in the process of developing (e.g., newborn skin or anagen skin). This is accomplished by enzymatic digestion by the use of trypsin, for example, to remove epidermis and collagenase, for example, to dissolve the dermis. The follicles are then purified.

Once the purified, developing follicles are obtained, the three-dimensional culture system may be set up. In particular, a culture dish is coated with, for example, collagen. The layer is then allowed to gel. The isolated follicles are then resuspended in, for example, collagen and Medium 199, and the mixture is plated over the initial collagen layer. This second layer is also given the opportunity to gel. Thus, a three-dimensional culture system is created in which the follicles are actually embedded in the second layer and maintain their functional and structural integrity.

Culture medium may then be added to the top of the culture. The medium may contain a number of components including, but not limited to antibiotics, Medium 199 and fetal bovine serum (FBS). Furthermore, the growth factors, discussed in more detail below, are also present in the culture medium added to the top of the culture. The medium may be changed daily, or as desired.

Two assays may then be carried out in combination with the model sytem. More specifically, using thymidine incorporation into the DNA present in the follicle, one may determine how the added growth factors affect cellular proliferation. Furthermore, one may also determine the effect of the growth factors on release of collagenolytic factors from the follicle cells. In this manner, one may determine the effect of any additive, for example, a pharmaceutical compound, on the proliferation and collagenase-secreting activity of a hair follicle cell.

As noted above, the relationship between a particular additive, for example, a growth factor, and cellular proliferation may be determined by measuring the quantity of cellular DNA synthesis as a function of radioactive thymidine incorporation. Thus, after the culture system has been established, the culture dish may be pulsed with $^3$[H] thymidine, for example. The follicles may then be released from the gel by enzymatic digestion, and the DNA present in the cells may be hydrolyzed. The DNA may then be measured by recording the presence of the radioactive thymidine. Thus, there is a direct relationship between the amount of thymidine incorporated and the amount of DNA synthesized, and therefore the amount of proliferation which has taken place.

Compounds other than radio-labeled thymidine can be utilized such as, for example, any DNA precursor which is labeled with or bound to a flourescent compound or other type of marker, or any other similar reagent which can detect DNA synthesis.

In order to determine the effect of an additive, for example, a growth factor, on the release of collagenase from the follicle, $^3$[H] collagen may be added to the first collagen gel layer present in the culture dish. The follicles can then, as described above, be resuspended in a second layer of collagen, and the mixture can be plated over the first layer. A liquid medium containing, for example, a growth factor will then be added to the top of the second layer. If collagenase is released, the bottom gel will be lysed, and the $^3$[H] collagen will be digested and released in a soluble form in the cultured medium. The percent of release of $^3$[H] collagen from the bottom layer is then calculated based on the total release which results from addition of purified bacterial collagenase. In this manner, it is possible to determine the effect of the additive on the collagenolytic activity released by the follicles.

These two assays, in combination with the 3-dimensional culture system, represent methods by which to study the response of a hair follicle to an exogenous compound. The results obtained by the use of these methods are discussed in more detail below.

Cell Proliferation

Figure 2:
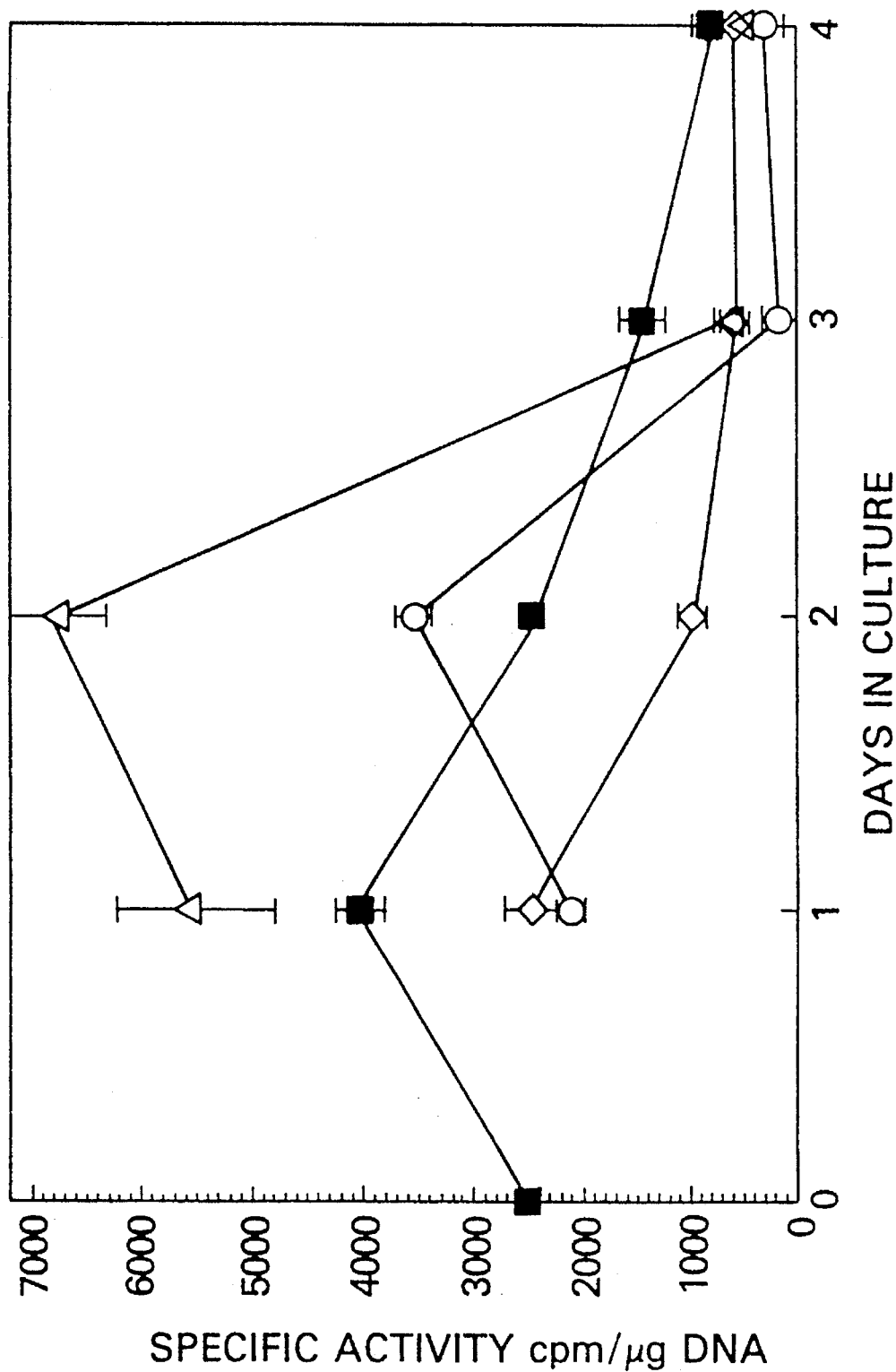
FIG. 2 show the opposing effects of supplemented growth factors on thymidine incorporation into hair follicle cells. Hair follicle cultures were fed daily with either control medium (closed squares), TGF-α (50 ng/ml, triangles), TGF-β2 (1 ng/ml, diamonds), or a combination of the two (circles). Each day dishes were pulse-labelled with [$^3$H]thymidine (5 µCi/ml) for 2 hours, following which follicles were released from the gel by collagenase digestion, washed, pelleted and frozen. At termination of the timepoints, the frozen pellets were analyzed for DNA content and incorporation of label into DNA. Error bars represent the range of duplicate dishes.

As can be observed based on FIGS. 1–3, cell proliferation, confined to the peripheral cells of the folliculoids, is stimulated by the growth factors EGF and TGF-α, and inhibited by TGF-β. (See Example 1). In combination, TGF-β inhibits the stimulatory response to TGF-α and EGF. Since the culture medium is supplemented with 8% fetal bovine serum, the effects of added growth factors are above those already present in serum. Plating density in the folliculoid culture model can alter the profile of the proliferation curve even though organoid contact does not occur. At high plating input (one dermal equivalent per 60 mm dish), DNA synthesis peaks after 24–48 hours and then reverts to a low maintenance value. At lower input (one half to one third dermal equivalent per 60 mm dish), DNA synthesis increases over 3–5 days before dropping to a low value. The reduction in DNA synthesis after 1–5 days in vitro is not an indication that the folliculoids have lost viability. Cultures are metabolically active for more than a week and secrete proteases for up to 12 days. Cultured follicles can be transplanted after 8 days and produce a haired skin (Rogers et al., supra). The relationship of the shape of the growth curve to the number of follicles plated could be due to nutrient depletion or accumulation of inhibitory substances including cytokines such as TGF-β. Nevertheless, the response to added growth factors is identical in high density and low density cultures both with regard to growth effects and protease secretion. It remains to be determined whether plating density can modify other aspects of follicle biology such as expression of markers of hair differentiation.

In addition to the results discussed above, the present invention has revealed new information concerning the composition of cultured folliculoids. Based on cytokeratin staining for K14 and K6, cells characteristic of inner and outer root sheath and follicle matrix are contained in the organoids. These components along with dermal papilla are essential for hair follicle growth and hair differentiation in vivo (Sengal, P., supra). Their presence together in the culture model supports the potential usefulness of this system to study the factors responsible for hair follicle development. Additional studies indicate that dermal papilla cells reside in many of the folliculoids.

It is important to note that the proliferative population of cultured follicle organoids is limited to the outer root sheath cells (K14, positive and K6 negative), and this is also a cytokine responsive population. In the mature anagen follicle, proliferation is limited to the matrix cells of the lower bulb and the outer root sheath. Stimulation of growth in vitro by TGF-α increases the number of cells positive for both K14 and K6 either by induction of the cytokeratins in matrix cells or by positive selection of the K6/K14 population. It is interesting to note that the bulb area of developing follicles is positive for K14 in vivo while the outer root sheath and matrix cells of the bulb of mature follicles are devoid of K14. Virtually all cells of cytokine-stimulated follicles are K14 positive suggesting that they may be analogous to developing follicle cells.

Collagenolytic Activity

The present inventors have previously proposed that hair follicle development and the anagen phase of the hair cycle are similar to tumor formation in that they all require invasion into the stromal compartment (Rogers et al., supra). The degradation of collagen gels by cytokine stimulated cultured follicles indicates that proteases are secreted by follicle cells. Based on zymographic analysis of culture supernatants, TGF-α alone and in combination with TGF-β stimulates secretion of multiple forms of gelatinase activity. Results of zymography indicate the presence of both 92 kD add 72 kD gelatinases as well as lower molecular weight species which may represent interstitial collagenase and pump-1. TGF-α also appears to induce processing of the 92 kD, 72 kD and interstitial collagenases to their lower molecular weight active forms. These enzymes are known to cooperate in degrading a type I collagen matrix (Murphy et al., *Int. J. Cancer* 44: 757–60 (1989)). Their regulation may be important in downgrowth of the developing hair follicle through the dermis. The potential to secrete collagenases in response to growth factors might also be important in cutaneous wound healing.

Tissue sections of mouse skin containing anagen follicles demonstrate reactivity with antibody recognizing both the active and latent forms of the 72 kD collagenase. This reactivity is clearly seen throughout epithelial tissue of the hair bulb, but not the dermal papilla. It is also present in the leading edge of newly forming follicle buds. In culture, immunoreactivity for this collagenase is found in virtually all follicle epithelial cells. It is not limited to those cells incorporating thymidine. Immunoreactivity is substantially and uniformly enhanced by combined exposure to TGF-α and TGF-β, in apparently all epithelial cells. Because of the limitations of antibody specificity, data for the 92 kD collagenase is less secure but suggestive of a pattern of staining similar to the 72 kD collagenase.

In particular, the zymograms suggested that the 92 and 72 kD Type IV collagenases were the major species expressed by control follicles in vitro and their release was stimulated by cytokines which induce collagenolytic activity. Reduction in molecular weights of these bands in cytokine treated-cells was consistent with their enzymatic activation. These proteases were further examined by immunohistochemical analyses performed on developing follicles in vivo and cultured follicle organoids.

The epithelial component of hair follicles from newborn mouse skin uniformly reacts with antibody recognizing the 72 kD gelatinase both in tissue section and in culture. In vivo, staining is particularly intense in the area of the hair bulb migrating into the deeper dermis, but the leading edge of newly forming follicles is also intensely stained. The dermal papilla is not stained. The staining of the epidermis is largely non-specific as second antibody alone gives a similar pattern. In culture, there is uniform staining of follicle epithelial cells and staining is increased in cultures exposed to TGF-α and very intense in cultures treated with the combination of TGF-α and TGF-β2. The increase in staining is not confined to peripheral cells which are stimulated to proliferate but appears to involve all of the epithelial components of control and treated follicles. Currently available antibodies to the human 92 kD gelatinase do not recognize this band on Western blots of mouse follicle culture supernatants. By immunohistochemistry, weak 92 KD gelatinase staining of matrix and outer root sheath cells is detected. In cultured follicles, the 92 KD gelatinase antibody produces a pattern of staining in control and cytokine treated follicles similar to the 72 KD collagenase, but less intense. However, the poor cross reactivity of the antibody with mouse tissues limits the interpretation of these data. These combined in vivo and in vitro data implicate type IV collagenases/gelatinases in the normal development of that hair follicle. However, regulation of the extracellular activity of these enzymes is extremely complex. Multiple factors modulating type IV collagenolytic activity have been identified (Brown et al., *Cancer* (in press)) and include transcriptional regulation of enzyme synthesis, extracellular activation of latent proenzyme and down regulation of enzyme activity by specific inhibitors, such as the tissue inhibitors of metalloproteinases (TIMPs).

Specific growth factors or their receptors have been detected in and around the hair follicle with expression varying according to the stage of the hair cycle. It is likely, therefore, that they are involved in regulation of hair follicle growth and development. EGF receptors have been localized within specific areas of epidermal tissue undergoing morphogenesis. Basal cells of embryonic rat skin bind [$^{125}$I]EGF except in regions overlying dermal condensates, the earliest identifiable sign of hair follicle morphogenesis. Furthermore, epithelial cells of the migrating hair germ and anagen follicle bind [$^{125}$I]EGF specifically, with the exception of cells adjacent to the upper end of the dermal papilla (Green et al., *J. Invest. Dermatol.* 83: 118–23 (1984)). TGF-β1 is another candidate cytokine likely to be important in hair follicle morphogenesis. TGF-β1 was detected in mesenchyme surrounding the budding vibrissal follicles of embryonic mouse skin (Heine et al., *J. Cell Biol.*, 105: 2861–76 (1987)), noted as early as day 11 of gestation, before hair germs are evident. In situ hybridization studies of embryonic mouse vibrissal follicles have localized TGF-β1 mRNA to the epithelial component of developing follicles. This expression was first noted at day 12.5 gestation, and was seen to intensify as development progressed and to disappear in the mature follicle (Lehnert et al., *Development* 104: 263:73 (1988)). Likewise, mRNA for TGF-β2 has been detected in embryonic mouse dermis at day 15.5 of gestation. This expression was noted to wane one day later while simultaneously increasing in the differentiating epidermis and hair follicle (Pelton et al., *Development* 106: 759–67 (1989)). On the basis of these findings, autocrine and paracrine mechanisms involving TGF-β family members in the maintenance of skin tissue homeostasis have been proposed (Lehnert et al., supra, and Pelton et al., supra).

The involvement of proteases in follicle morphogenesis is also supported by studies in other tissues. The tissue remodeling occurring with parietal endoderm formation in the early mouse embryo, post-partum uterine involution, and involution of the mammary gland following lactation are influenced by proteases ((Laiho et al., *Cancer Res.* 49: 2533–53 (1989)). In skin, collagen fibrils have been noted in macrophages surrounding regressing hair follicles (Parakkal, R. F., *J. Ultrastruct. Res.* 29: 210–17 (1969)) suggesting active digestion and phagocytosis of matrix material. Furthermore, type I collagen is detected along the dermal/epidermal junction of interfollicular skin but is absent at the base of budding hair follicles and dermal condensates (Mauger et al., *Rouxs Arch. Dev. Biol.* 196: 295–302 (1987)), an indication of matrix destruction during active hair follicle development. Keratinocytes can also synthesize proteolytic enzymes (Grondahl-Hansen et al., *J. Invest. Dermatol.* 90: 790–95 (1988), Peterson et al., *J. Invest. Dermatol.* 92: 156–59 (1989) and Woodley et al., *J. Invest. Dermatol.* 86: 418–23 (1986)) although, in the 3-dimensional culture system, interfollicular keratinocytes did not release collagenases in response to cytokines. EGF is known to increase secretion of collagenase and plasminogen activator by human fibroblasts (Chua et al., *J. Biol. Chem.* 260: 5213–16 (1985) and Laiho et al., supra) although mouse fibroblasts did not respond to cytokines in the collagen gel by protease release but did respond by growth. Thus, individual or combined exposures to cytokines may yield unique responses dependent on species, cell type or culture conditions. These variations emphasize the importance of the model system when studying a physiological process in vitro.

The present results suggest that combinations of factors of the TGF-β and EGF families of growth factors may act to regulate cell proliferation and control protease release in the developing follicle. The present inventors have demonstrated that these cytokines can produce distinct effects when present in combination versus when present individually. The present inventors have further demonstrated that the responses in this hair follicle culture model are similar to known changes which occur during follicle development in vivo. This is encouraging for future studies designed to identify unique properties of hair follicle components, specific factors involved in stages of hair follicle development, and to identify reagents which could influence hair follicle biology.

In view of the above, the present invention is an important tool for the study of hair follicle physiology and for the detection of reagents which may stimulate hair growth. The development of the hair follicle, both during embryonic formation of the first follicles structures in the skin and repeatedly during hair cycles in the adult organism, is the rate limiting step in hair growth. Pathological or biological conditions where hair growth is abnormal (such as male baldness, alopecia areota, alopecia totalis, iatrogenic alopecia, e.g., after cancer chemotherapy) commonly involve failure of hair follicle growth and development, not hair differentiation. Thus, models to study hair follicle growth and development are essential for understanding the pathophysiology of hair-related problems and for identifying reagents (i.e., biologicals and pharmaceuticals) which might correct the problems. The present inventor and his colleagues have previously discovered a model which maintains the complex, three-dimensional structure of the developing follicle organoid so that appropriate cell interactions remain intact. These organoids contain cells of the outer root sheath, inner root sheath, hair matrix and dermal papilla, all of which are essential components of the follicle. This model, as described above, may be utilized in conjunction with two assays which may be applied to the analysis of the biological response of developing follicles to exogenous stimulation. The two assays reflect distinct processes essential for the growth and development of follicles either during fetal development or during the repeated hair cycles of post-natal life. The stimulation of DNA synthesis is a marker of the proliferative response required for hair follicle growth. The stimulation of protease activity is a requirement for downgrowth of the developing hair follicle into the stroma of the dermis. Together these assays may predict the influence of exogenous compounds on essential components of hair follicle growth and development. The above cytokine results, which were selected because of their reputed involvement in the process of hair follicle growth and development, indicate that the model and the assays are relevant to this process.

All of the above results indicate that individual reagents have selective influences on each of the responses studied herein. Furthermore, responses from combined exposures may be different than individual exposures. This observation has very important implications for the study of hair growth and the analysis of pharmaceuticals which may influence hair growth.

The present invention can be illustrated by the use of the following non-limiting examples.

EXAMPLE I

Effect of Growth Factors on Follicle Cell Proliferation

Growth Factors and Chemicals: TGF-β1 and TGF-β2 from human platelets were gifts of Dr. Michael Sporn (National Cancer Institute, Bethesda, Md.). Rat synthetic transforming growth factor alpha (TGF-α) was purchased from ICN Biochemicals (Cleveland, Ohio); cholera toxin (CT) from List Biological Laboratories, Inc. (Campbell, Calif.), and epidermal growth factor (EGF) from Collaborative Research (Lexington, Mass). [$^3$H]thymidine (5 Ci/mmole) was purchased from Amersham Corporation (Arlington Heights, Ill.) and [$^3$H]collagen (rat type I, N-[propionate-2-3-$^3$H]propionylated) from New England Nuclear/Dupont (Wilmington, Del.).

Isolation of hair follicles Follicles were released from the skin of 3–5 day old Balb/c mice by trypsin and collagenase digestion as previously described (Rogers et al., supra). Follicles were purified by centrifugation through 9% Ficoll (Pharmacia), at 800 rpm for 5 min in a tabletop clinical centrifuge, and washed 3–5 times with Medium 199 before plating.

Culture Methods: Hair follicles were cultured as described previously (Rogers et al., supra). In brief, cultures utilized a matrix of type I collagen (Vitrogen, Collagen Corporation, Palo Alto, Calif.), neutralized with NaHCO3 and diluted 9:1 with 10× Medium 199 (Media Services, NIH). Dishes were coated with 2% collagen; follicles or cell pellets were resuspended in Medium 199 (Media Services, NIH) and collagen to a final concentration of 1.8% collagen, and layered onto the coated surface. Each layer was allowed to gel 20 min. at 370° C. Cultures were fed from above and incubated in a 7% $CO_2$ atmosphere. Culture medium was Medium 199 containing 3.25 g/l $NaHCO_3$, 0.8% Antibiotic-Antimycotic Solution (GIBCO, Grand Island, N.Y.) and 0.8 mM $CaCl_2$, supplemented with 8% FBS and growth factors as noted. The entire yield of hair follicles from one mouse dermis was plated in 2.5 ml collagen suspension per 60 mm dish, unless otherwise noted. For determination of collagenase release, dissociated cells were plated at a final concentration of $8 \times 10^6/2.5$ ml collagen/60 mm dish. To determine thymidine incorporation into fibroblasts, freshly isolated fibroblasts were plated at a final concentration of $2 \times 10^6/2.5$ ml collagen/60 mm dish. At the end of each experiment, cells or follicles were released from the gel by a 20 min incubation with 0.035% collagenase (class I, Worthington Biochemical, Freehold, N.J.) in culture medium.

Thymidine Incorporation: Medium was changed daily in all assays. At each timepoint, duplicate dishes were pulsed for 2 hr with 5 μCi/ml $^3$H]thymidine. Cells were released from the gel by collagenase digestion, washed in pBS containing 1% thymidine, and pellets stored at −20° C. At the end of each time course, pellets were washed 2× with 0.2N perchloric acid (PCA) and lysed with 1N NaOH; macromolecules were precipitated and washed once with 0.5N PCA. The DNA was hydrolyzed at 90° C., in a 20 min reaction with 0.5N PCA, and duplicate aliquots were counted or reacted with diaminobenzoic acid dihydrochloride (Aldrich Chemical Co.) for quantitation of DNA (Bowden et al., *Chem. Biol. Interact.* 8: 379–94 (1974)). DNA was measured on a fluorescence spectrophotometer (Perkin-Elmers model #650-103) using excitation and emissions wavelengths of 410 and 500 nm, respectively. Results are presented as cpm [$^3$H]thymidine incorporated per μg DNA±range of duplicate dishes. Results are from a single representative experiment repeated ≧2 times.

Previous results on the time dependent incorporation of [$^3$H]thymidine into cultured hair follicle cells demonstrated a gradual increase in thymidine incorporation, with maximal activity occurring at day 3–5 and returning to baseline by day 8 (Rogers et al., supra). In the current experiments, follicle DNA synthesis peaks within the first 24–48 hours in culture, and declines thereafter (FIG. 1). This curve is determined in part by culture conditions. Follicles plated at one-third the standard density of one dermal equivalent per 60 mm dish (the entire follicle yield from the dermis of one newborn mouse skin equals one dermal equivalent) follow a thymidine incorporation curve more similar to our previous study (FIG. 1) where one-half dermal equivalent per dish was used (Rogers et al., supra).

Figure 3A:
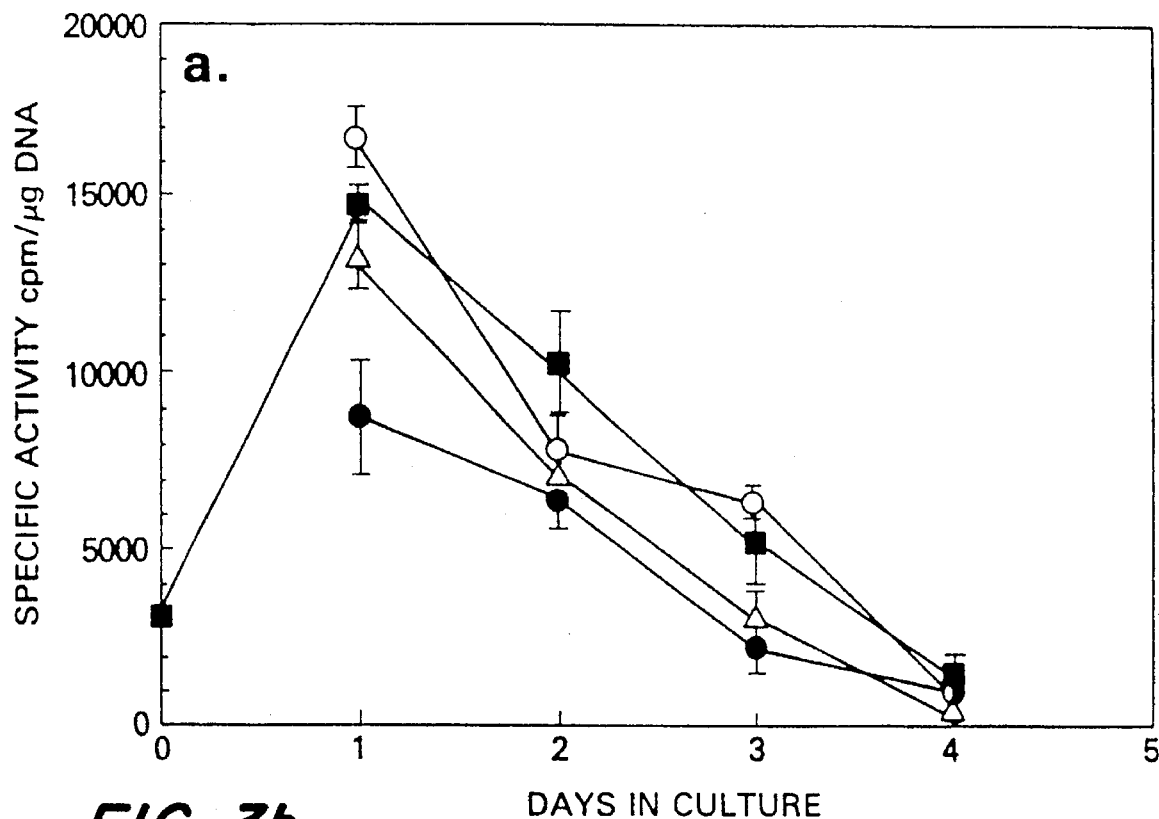
FIGS. 3a and b show the effects of varying TGF-β2 dose on thymidine incorporation into cells in collagen gel culture. a. Hair follicles and b. fibroblasts were cultured with Medium 199 (closed squares), or TGF-β2 at concentrations of 0.1 ng/ml (open circles), 0.5 ng/ml (open triangles) or 1.0 ng/ml (closed circles).
Figure 3B:
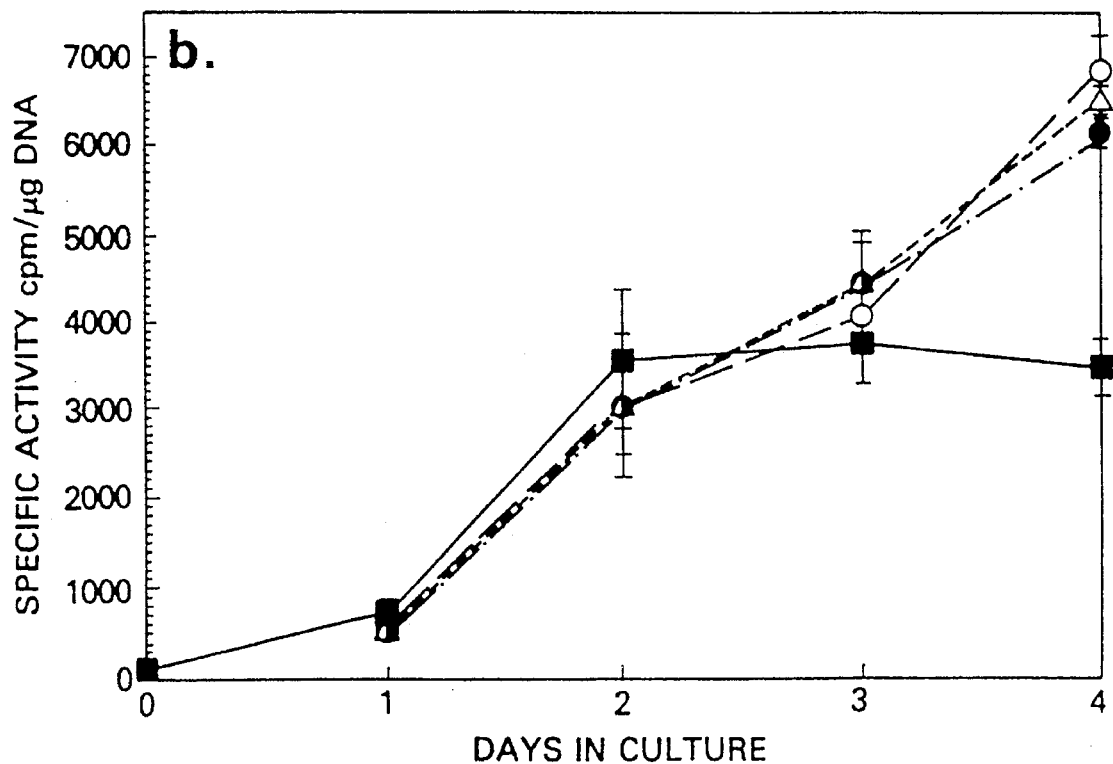

EGF was shown previously to stimulate follicle DNA synthesis although it did not change the pattern of incorporation from that of control follicles (Rogers et al., supra). The data in FIG. 2 indicate that TGF-α also increases follicle thymidine incorporation without a substantial alteration in the shape of the DNA synthesis curve of control cells. A dose response study (not shown) indicated that 1 ng/ml TGF-α had no demonstrable effect on thymidine incorporation after 24 hours in culture whereas doses of 10, 25 and 50 ng/ml yielded a 57%, 65% and 110% increase incorporation of label over control cultures, respectively. Both TGF-β1 and TGF-β2 suppress thymidine incorporation in hair follicle preparations at concentrations of 0.5 and 1 ng/ml (shown for TGF-β2: FIG. 3a, FIG. 2). TGF-β2 added at a dose of 0.1 ng/ml and 0.01 ng/ml (not shown) had no effect on thymidine incorporation in these cells. In addition TGF-β1 and TGF-β2 suppress the stimulation of thymidine incorporation observed with TGF-α (FIG. 2). The same patterns of pharmacological responses were seen in cultures plated at lower density (not shown), but extended DNA synthesis profile as noted in FIG. 1. Since hair follicle preparations contain some contaminating dermal fibroblasts, thymidine incorporation was studied in collagen matrix cultures of isolated fibroblasts to assess their contribution to the growth curve. Fibroblasts incorporate little [$^3$H]thymidine on day 1 and increase incorporation to a plateau value on subsequent days. Unlike the suppression observed with TGF-β2 in follicle preparations, the cytokine enhances [$^3$H]thymidine incorporation in fibroblast cultures at all doses tested (FIG. 3b). Thus, TGF-β inhibition of [$^3$H]thymidine incorporation in hair follicle cultures is not due to cytokine-mediated growth inhibition of this contaminating subpopulation.

Freshly isolated pelage follicles from 3–5 day old mice appear as elongated cell clumps under phase morphology, some with a well-developed central hair. The organoids enlarge during culture and after several days the follicles develop dense centers. The organoids become spherical as cells grow outward from the bulb region into the surrounding gel matrix and along the hair shaft. However, the original 3-dimensional structure is still evident. In contrast, follicles incubated with TGF-α or EGF form cell sheets of new outgrowth and coalescing units, in part due to structural changes in the gel (see below for explanation). Hair follicles incubated with TGF-β look similar to those grown under control conditions. Commonly, isolated dendritic cells are seen in these cultures. These probably represent fibroblasts or melanocytes which spread in the gel rather than remain as rounded cells. Similar cell types were seen in fresh fibroblast cell preparations under these growth conditions. Follicles incubated with combinations of TGF-α or EGF and TGF-β also form sheets which are flatter than the outgrowths with TGF-α alone.

Autoradiography: Following label with [$^3$H]thymidine, fragments of collagen gel containing cells were washed extensively in PBS containing 1% thymidine, fixed in 70% EtOH, and embedded in paraffin. Three μm thick sections were mounted on glass slides, and dipped in NTB2 emulsion (Eastman Kodak, Rochester, N.Y.) at 42° C. (diluted 1:1 in water). Sections were exposed 3 days, developed in Dektol developer (Eastman Kodak), and fixed with Kodak fixer. Cells were counterstained with Gill's hematoxylin.

Hair follicles are complex cellular organoids in which specific subpopulations of cells perform specialized functions, including proliferative responses. To determine if [$^3$H]thymidine incorporation was a general or specific response in cultured follicles, sections of [$^3$H]Thymidine labelled follicles were examined by autoradiography. The cells within the hair follicle which undergo DNA synthesis in culture appear limited to the periphery of the follicle structure, and are presumably outer root sheath cells. A higher degree of labelling was incubated with TGF-α, and labelled nuclei, observed in cultures as in control cultures, were predominantly in peripheral cells. Few cells were labelled in cultures incubated with TGF-β; cultures treated with the combinations of TGF-α and -β displayed an intermediate labelling pattern, also in nuclei of peripheral cells.

Outer root sheath cells are believed to be the source of germinative cells which initiate the hair cycle (Sengel et al., supra). The autoradiographs suggested functional specialization was sustained in the culture model. This was further supported by immunohistochemical studies of cultured follicles. Keratin 14 is a marker of cells in the upper follicle column and the outer root sheath surrounding the matrix region, but not the matrix cells (FIG. 6E) (Coulombe et al., *J. Cell Biol.* 109: 2295–312 (1989) and Stark et al., *Differentiation* 35: 236–48 (1987)). In culture a pattern of staining is maintained whereby putative matrix cells, negative for K14, are adjacent to a layer or column of K14 positive cells. After treatment with TGF-α or TGF-α plus -β, K14 positive cells are more abundant and diffusely distributed, suggesting a selection for this population is occurring or the protein is induced. Similar results are seen with the keratin 6 marker. This cytokeratin is expressed either by an inner layer of outer root sheath cells or by inner root sheath cells in the upper part of the follicle (Coulombe et al., supra, Lynch et al., *J. Cell Biol.* 103: 2593–606 (1986) and Coulombe et al., supra). In culture, the limited distribution of K6 positive cells resembles the in vivo structure, and only a subpopulation is positive for both K6 and K14 treatment pairs are serial sections). Cytokine treatment increases the number of K6 positive cells to coincide with the K14 positive population. These results suggest that the culture model comprises cells of the inner and outer root sheath and matrix cells, and these maintain their phenotype and special response pattern at least within the limits of the markers studied. However cytokine treatment can alter either the distribution of cells or marker expression.

EXAMPLE II

Effect of Growth Factors on Collagenase Release

Culture dishes were coated with 2 ml of 2% collagen gel containing 0.5 μCi [$^3$H]collagen and follicles were plated as Example I. At each feeding, the medium was collected, measured, and duplicate aliquots were counted. At the end of each experiment the remaining gel was digested with 0.035% collagenase, duplicate aliquots were counted, and the percent of release of [$^3$H] collagen from the bottom layer was determined. In order to compare the response of hair follicles to other major skin cell types, dermal fibroblasts or interfollicular epidermal cells were isolated as previously described (Rogers et al., supra and Yuspa, S. H., "Methods for the use of epidermal cell culture to study chemical carcinogenesis," In: *Methods in Skin Research* (S. Kerrow et al., (eds) pp. 213–49 (1985)) and incorporated into 1.8% collagen top gels. Immature hair follicles and cell clumps were removed from the interfollicular epidermal cell suspension by low speed centrifugation (400 rpm, 3 min in a tabletop centrifuge). Results are presented as mean % [$^3$H] collagen released from culture gel, ±range of duplicate dishes. Results are from a single representative experiment; each assay was repeated ≧2×.

Figure 4:
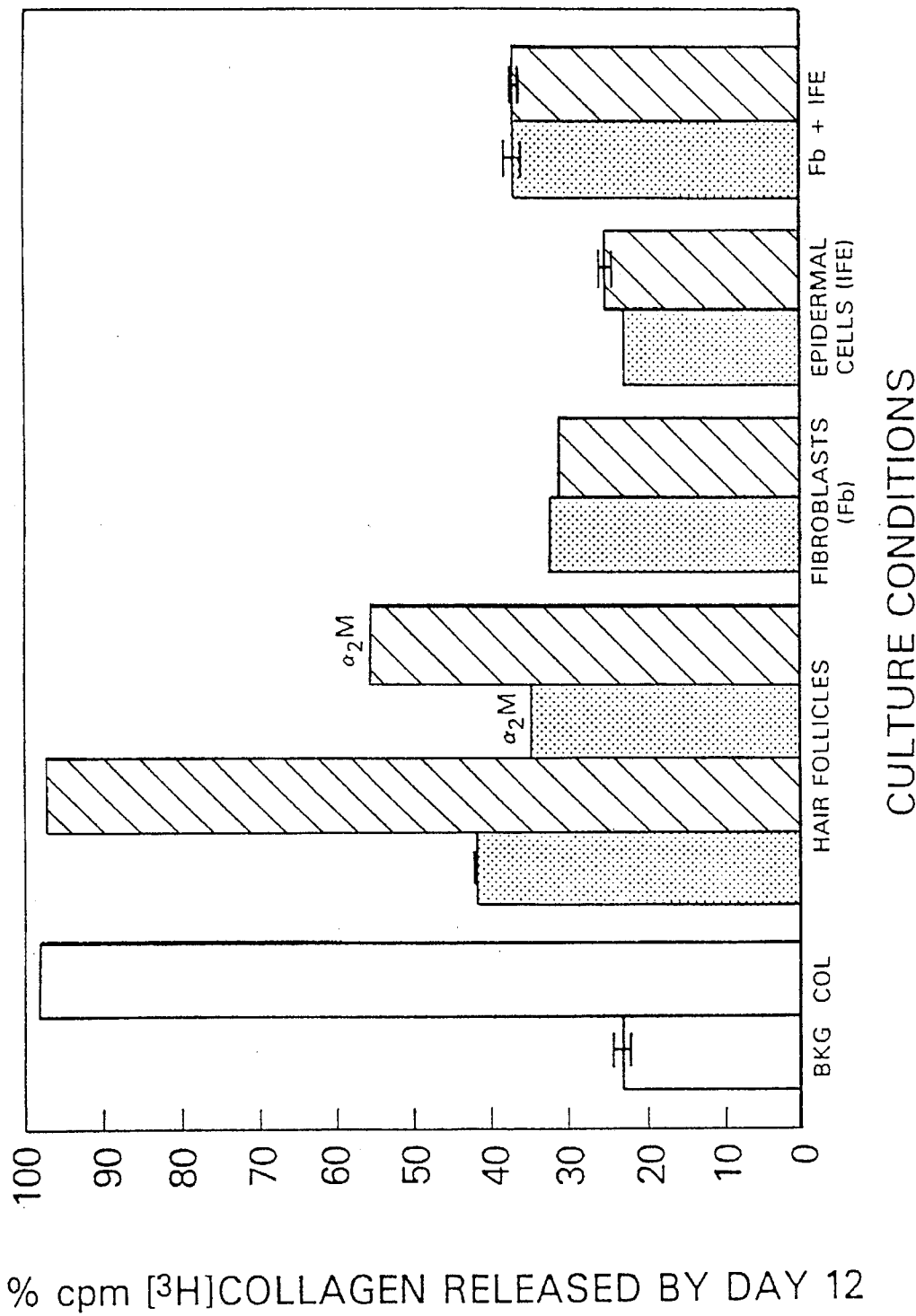
FIG. 4 shows the release of collagenolytic activity from skin-derived cells in collagen gel. Hair follicles, dermal fibroblasts and interfollicular epidermal cells were cultured without (stippled bars) and with (solid bars) 50 ng/ml EGF added to culture medium. Alpha-2-macroglobulin ($α_2M$) was added to medium as noted at a concentration of 10 µg/ml. [$^3$H]collagen was incorporated into the lower collagen gel layer, and cells were plated in the upper layer. Culture medium (2.5 ml), supplemented as noted, was layered over the top collagen layer containing cells. Medium was changed after 1 and 4 days. Following 12 days culture medium was collected and the remaining gel was digested with collagenase. Volumes of the medium and digested gels were measured and duplicate 100 µl aliquots of each were counted. Total cpm released and remaining in each gel was calculated based on volume measurements. [$^3$H]collagen released is presented as % of total cpm incorporated into the bottom gel layer. Open bars represent gels contains no cells and incubated with either control medium (BKG) or 0.035% collagenase (COL). Error bars represent range of duplicate samples.

Based on the results discussed above, it is apparent that hair follicles cultured in a collagen I matrix do not noticeably lyse the gels after 7–14 days. However, when gel lysis is monitored radiochemically as the release of [$^3$H]collagen incorporated into a lower gel matrix, cell mediated lysis can be measured relative to gels without cells (FIG. 4). This suggests that hair follicles release a low level of a diffusible proteolytic factor, most likely a collagenase. EGF enhances the release of this collagenolytic activity from hair follicle cells in culture at an added dose of 25 ng/ml to medium (final supplemented dose: 8.3 ng/ml) (FIG. 4). Single cell suspensions of interfollicular epidermal cells plated in collagen gel cause no detectable release of [$^3$H]collagen from the gel, with or without added EGF. There is a small release of [$^3$H]collagen from gels containing primary fibroblast preparations plated as single cell suspensions and from gels containing fibroblasts and epidermal cells in combination, but no further stimulation of this release in response to EGF. Thus, this response is specific for hair follicles. Alpha-2-macroglobulin ($\alpha_2$M) binds covalently to collagenase and is an abundant inhibitor of collagenase activity in vivo (Laiho et al., Cancer Res. 49: 2533–53 (1989) & Sottrup-Jensen et al., J. Biol. Chem. 264: 393–401 (1989)). The lysis of the collagen gel by hair follicles in response to EGF is reduced by the addition of $\alpha_2$M (FIG. 4).

Figure 5:
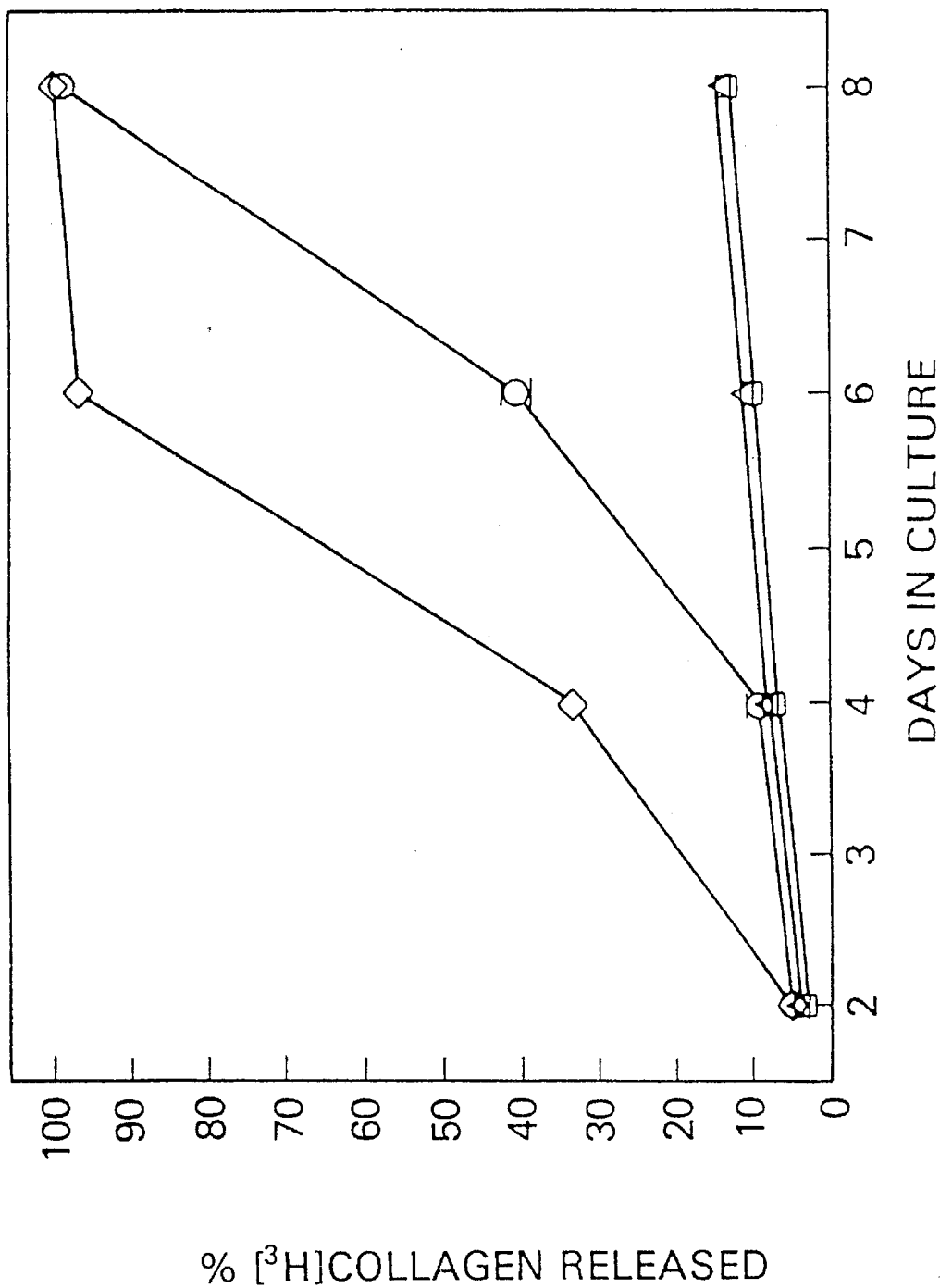
FIG. 5 shows the synergistic effects of growth factors on release of collagenolytic activity from hair follicle cells: time course. [$^3$H]collagen was incorporated into the lower collagen gel layer and hair follicles were plated in the upper layer. Control culture medium (□) or medium supplemented with 50 ng/ml TGF-α (0), 1.0 ng/ml TGF-β2 (Δ) or both (◊) was layered over the top collagen layer containing cells. Medium was collected and changed every 2 days; on day 8 the remaining gels were digested with collagenase. Volumes of medium from each collection and digested gels were measured and duplicate 100 µl aliquots counted. Cumulative cpm released from the bottom gel layer were determined for each timepoint.

Like EGF, TGF-$\alpha$ increases secretion of collagenolytic activity. While TGF-$\alpha$ concentrations of 10 and 25 ng/ml are required to enhance DNA synthesis, gel lysis is not detected at these doses when assayed by the radiochemical release assay (not shown). At 50 ng/ml, TGF-$\alpha$ causes substantial lysis by day 6 and complete lysis by day 8 (FIG. 5). Collagenolytic activity from hair follicle preparations is not enhanced by TGF-$\beta$1 or TGF-$\beta$2 (FIG. 5). In contrast to the TGF-$\beta$ mediated suppression of EGF or TGF-$\alpha$ stimulated thymidine incorporation (see FIG. 2), TGF-$\beta$1 and TGF-$\beta$2 interact synergistically with either EGF or TGF-$\alpha$ in stimulating the release of collagenase from hair follicle cells. Gel lysis is enhanced by 4 days and complete by 6 days when follicles are cultured with a combination of TGF-$\alpha$ and TGF-$\beta$2 (FIG. 5). Identical results were seen with TGF-$\beta$1 and TGF-$\alpha$. Furthermore, a significant increase in release of [$^3$H]collagen is observed at lower doses of TGF$\alpha$ or EGF when TGF-$\beta$ is present in the growth medium (FIG. 6). To determine whether secretion of collagenolytic factors could be induced by other agents which stimulate intracellular signalling pathways working in combination with TGF-$\beta$, follicles were cultured with cholera toxin in the presence and absence of added TGF-$\beta$, and release of radiolabelled collagen from the lower gel was monitored. Cholera toxin is a potent mitogen of cultured hair follicle cells, and by itself has no apparent effect on release of collagenolytic activity from hair follicle preparations (Rogers et al., supra). No detectable synergy was seen between TGF-$\beta$1 or TGF-$\beta$2 and cholera toxin (not shown).

EXAMPLE III

Characterization of Collagenolytic Activity

Zymography: Aliquots of culture supernatants were separated on 10% SDS-polyacrylamide gels containing 0.1% gelatin (Novex, Encinitas, Calif.) as previously described (Harssen et al., Anal. Biochem. 102: 196–202 (1980)). Following removal of SDS from the gel by incubation in Triton X-100 (2.5%, v/v) for 30 minutes, gels were incubated for 6 hours at 37° C. in 50 mM TrisHCl pH 7.6 containing 0.2M NaCl, 5 mM CaCl$_2$ and 0.02% Brij-35 (w/v) and stained with Coomassie Blue. Light areas indicate the presence of gelatin-degrading enzymes. Supernatants of cell lines HT1080 and A2058, whose profiles of collagenase secretion have been characterized (Brown et al., Cancer Res. (in press) and Stetler-Stevenson et al., J. Biol. Chem. 264: 1353–56 (1989)), were included as controls.

To characterize the nature of the collagenolytic activity released by treated and control follicles, culture supernatants were collected and analyzed by zymography (see above). Follicle organoids cultured in Medium 199 secrete basal levels of gelatinolytic activity migrating at molecular weights consistent with the latent forms of the 92 kD and 72 kD gelatinases/type IV collagenases, [15]. TGF-$\beta$2 does not significantly alter this pattern, whereas TGF-$\alpha$ causes a marked increase in these two gelatinases and induces slightly lower molecular weight species consistent with the activated forms of these proenzymes (Brown et al., Cancer Res. (in press) & Stetler-Stevenson et al., J. Biol. Chem, 264: 1353–56 (1989)). TGF-$\alpha$ also induces new lower molecular weight species consistent with known sizes of interstitial collagenase and pump-1 (Quantin et al., Biochemisty 28: 5327–34 (1989)). TGF-$\beta$2 added to cultures simultaneously with TGF-$\alpha$ results in further increases in all of these activities. A 10 mM EDTA buffer completely inhibited gel clearance in a duplicate Zymogram, confirming that these bands of activity are due to metalloproteinases. Since total cell numbers (as measured by DNA/culture) do not increase in TGF-$\alpha$/TGF-$\beta$ cultures, and increase no more than 2 fold in TGF-$\alpha$ cultures, the increase in collagenolytic activity cannot simply be due to more cells these cultures. Furthermore, cholera toxin is a more potent follicle mitogen than TFG-$\alpha$, yet does not increase collagenolytic activity.

EXAMPLE IV

Antibody Binding

Antibodies: Monospecific rabbit antibodies recognizing mouse keratins 6 and 14 have been previously described (Roop et al., Cancer Res. 48: 3245–52 (1988) and Roop et al., "Sequential Changes in Gene Expression During Epidermal Differentiation", In: The Biology of Wool and Flair, Rogers et al. (eds) pp. 311–324 (1989)). Monospecific rabbit antibody to the human 72 kD collagenase was directed to a sequence present in both latent and active forms of this enzyme (Monteagudo et al., Am. J. Path. 136: 585–89 (1990) ans Stether-Stevenson et al., J. Bio. Chem. 264: 1353–56 (1989)).

Immunohistochemistry: Deparaffinized EtOH fixed sections from newborn mouse skin or cultured follicles were pre-treated for 20 minutes at room temperature with normal goat serum before overnight incubation at room temperature with primary rabbit antibodies against keratin 6, keratin 14 and the 72 kD type IV collagenase. Antibody binding was visualized by horseradish peroxidase staining using the HistoMark Streptavidin HRP System and HistoMark Orange staining kit (Kirkegaard and Perry, Gaithersburg, Md.). Since cultured follicles are randomly oriented in collagen gels, histological sections contain a variety of shapes and sizes.

What is claimed is:

1. A method for determining hair follicle cell proliferation in response to a chemical agent comprising the steps of:
   i) isolating hair follicles from dermis;
   ii) plating a layer of semi-solid medium on a support;
   iii) mixing said follicles with a semi-solid medium, and plating said mixture over the layer of step (ii), thereby creating a three-dimensional culture system;
   iv) adding a chemical agent to a liquid medium placed over the semi-solid medium of step (iii);
   v) pulsing said three-dimensional culture system with a radio-labeled compound or reagent which can detect DNA synthesis;
   vi) releasing cells from said follicles from the layer in which they are embedded, by enzymatic digestion; and
   vii) measuring the amount of cellular proliferation by determining the amount of said radio-labeled compound or reagent incorporated into the DNA of said cells.

2. The method of claim 1 wherein said chemical agent is a growth factor or pharmaceutical.

3. The method of claim 2, wherein said growth factor is selected from the group consisting of EGF and cholera toxin.

4. The method of claim 2 wherein said growth factor is selected from the group consisting of TGF-α, TGF-β1, and TGF-β2.

5. The method of claim 1 wherein said radio-labeled compound or reagent is a DNA precursor.

6. The method of claim 5 wherein said radio-labeled compound or reagent is tritiated thymidine.

7. The method of claim 1 wherein said layer of step (ii) comprises collagen.

8. A method for detecting the effect of a chemical agent on the release of lytic factors from hair follicle cells comprising the steps of:
   i) isolating hair follicles from dermis;
   ii) plating a layer of semi-solid medium, comprising a radio-labeled agent, on a support;
   iii) mixing said follicles with a second semi-solid medium, and plating said mixture over the layer of step (ii), thereby creating a three-dimensional culture system;
   iv) adding said chemical agent to a liquid placed over the semi-solid medium of step (iii); and
   v) determining the percentage of the radio-labeled agent released from said layer of step (ii), thereby determining the ability of said follicle cells to release lytic factors.

9. The method of claim 8 wherein said chemical agent is a growth factor or pharmaceutical.

10. The method of claim 9 wherein said growth factor is selected from the group consisting of EGF and cholera toxin.

11. The method of claim 9 wherein said growth factor is selected from the group consisting of TGF-α, TGF-β1, and TGF-β2.

12. The method of claim 8 wherein said radio-labeled agent of step (ii) is tritiated collagen.

13. The method of claim 8 wherein said layer of step (ii) comprises collagen.

14. The method of claim 8 wherein the lytic factors of step (v) are collagenolytic.

15. A method for determining non-human hair follicle cell proliferation in response to a chemical agent comprising the steps of:
   i) isolating hair follicles from non-human mammalian dermis;
   ii) plating a layer of semi-solid medium on a support;
   iii) mixing said hair follicles with a semi-solid medium, and plating said mixture over the layer of step (ii), thereby creating a three-dimensional culture system;
   iv) adding a chemical agent to a liquid medium placed over the semi-solid medium of step (iii);
   v) pulsing said three-dimensional culture system with a radio-labeled compound or reagent which can detect DNA synthesis;
   vi) releasing said hair follicle cells from the layer in which they are embedded, by enzymatic digestion; and
   vii) measuring the amount of cellular proliferation by determining the amount of said radio-labeled compound or reagent incorporated into the DNA of said cells.

16. The method of claim 15 wherein said chemical agent is a growth factor or pharmaceutical.

17. The method of claim 16 wherein said growth factor is selected from the group consisting of EGF and cholera toxin.

18. The method of claim 16 wherein said growth factor is selected from the group consisting of TGF-α, TGF-β1, and TGF-β2.

19. The method of claim 15 wherein said radio-labeled compound is a DNA precursor.

20. The method of claim 15 wherein said layer of step (ii) comprises collagen.

21. A method for detecting the effect of a chemical agent on the release of lytic factors from non-human hair follicle cells comprising the steps of:
   i) isolating hair follicles from non-human mammalian dermis;
   ii) plating a layer of semi-solid medium, comprising a detectable agent, on a support;
   iii) mixing said hair follicles with a semi-solid medium, and plating said mixture over the layer of step (ii), thereby creating a three-dimensional culture system;
   iv) adding said chemical agent to a liquid placed over the semi-solid medium of step (iii); and
   (v) determining the percentage of the detectable agent released from said layer of step (ii), thereby determining the ability of said hair follicle cells to release lytic factors.

22. The method of claim 21 wherein said chemical agent is a growth factor or pharmaceutical.

23. The method of claim 22 wherein said growth factor is selected from the group consisting of EGF and cholera toxin.

24. The method of claim 22 whereon said growth factor is selected from the group consisting of TGF-α, TGF-β1, and TGF-β2.

25. The method of claim 21 wherein said detectable agent is a radio-labeled nucleotide.

26. The method of claim 21 wherein said layer of step (ii) comprises collagen.

27. The method of claim 21 wherein the lytic factor of step (v) is collagenolytic.

* * * * *